United States Patent
Erhard et al.

(10) Patent No.: US 12,226,245 B2
(45) Date of Patent: Feb. 18, 2025

(54) X-RAY POSITION TRACKING

(71) Applicant: KONINKLIJKE PHILIPS N.V., Eindhoven (NL)

(72) Inventors: Klaus Alfred Erhard, Hamburg (DE); Heiner Daerr, Hamburg (DE); Artur Sossin, Hamburg (DE); Axel Thran, Hamburg (DE); Bernhard Johannes Brendel, Norderstedt (DE); Christian Haase, Hamburg (DE); Claas Bontus, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 117 days.

(21) Appl. No.: 18/017,143

(22) PCT Filed: Jul. 16, 2021

(86) PCT No.: PCT/EP2021/070004
§ 371 (c)(1),
(2) Date: Jan. 20, 2023

(87) PCT Pub. No.: WO2022/023082
PCT Pub. Date: Feb. 3, 2022

(65) Prior Publication Data
US 2023/0263487 A1    Aug. 24, 2023

(30) Foreign Application Priority Data
Jul. 30, 2020 (EP) .................................. 20188576

(51) Int. Cl.
*A61B 6/12* (2006.01)
*A61B 6/00* (2006.01)

(52) U.S. Cl.
CPC .............. *A61B 6/12* (2013.01); *A61B 6/4441* (2013.01); *A61B 6/52* (2013.01)

(58) Field of Classification Search
CPC ........... A61B 6/12; A61B 6/4441; A61B 6/52; A61B 6/032; A61B 2090/3966; A61B 6/482; A61B 6/5205; A61F 2/852
See application file for complete search history.

(56) References Cited

U.S. PATENT DOCUMENTS

| 7,656,996 B2 | 2/2010 | Harding et al. |
| 10,139,354 B2 | 11/2018 | Persson |
(Continued)

FOREIGN PATENT DOCUMENTS

WO    2019144065 A1    7/2019

OTHER PUBLICATIONS

Qi et al., "X-ray Spectral Imaging Program: XSIP,", Journal of Synchrotron Radiation, vol. 27, pp. 1734-1740. (Year: 2020).*
(Continued)

*Primary Examiner* — Kiho Kim

(57) ABSTRACT

A spectral X-ray imaging system (100) includes an X-ray source (110) and an X-ray detector (120) that are mounted to a support structure (150). The support structure (150) is configured to rotate the X-ray source (110) and the X-ray detector (120) around two or more orthogonal axes (A-A', B-B'). One or more processors (130) are configured to cause the system (100) to perform operations that include: generating a spectral image based on the spectral image data; and identifying, in the spectral image, a position of a first fiducial marker (180$i$) comprising a first material, based on a first X-ray absorption k-edge energy value (190$i$) of the first material.

15 Claims, 2 Drawing Sheets

(56) References Cited

U.S. PATENT DOCUMENTS

| | | |
|---|---|---|
| 10,231,684 B2 | 3/2019 | Lin et al. |
| 2010/0067771 A1 | 3/2010 | Dahnke et al. |
| 2017/0023496 A1 | 1/2017 | Persson |
| 2017/0119555 A1 | 5/2017 | Bayer |
| 2018/0114314 A1 | 4/2018 | Butler et al. |

OTHER PUBLICATIONS

Magistro et al., "Optimized management of urolithiasis by coloured stent-stone contrast using dual-energy computed tomography (DECT)", BMC Urology, 19-29, (2019).

Johnson et al., "Dual-energy CT for the evaluation of silicone breast implants", Eur Radiol, 23, pp. 991-996, (2013).

Sigovan et al., "Feasibility of improving vascular imaging in the presence of metallic stents using spectral photon counting CT and K-edge imaging", Scientific Reports, 9, (2019).

Schirra et al., "Quantitative image feedback in TACE-combining novel imageable beads and spectral CT", Scientific Sessions, (2013).

Si-Mohamed et al., "Review of an initial experience with an experimental spectral photon-counting computed tomography system", Nuclear Instruments and Methods in Physics Research, A, 873, (2017), 27-35.

http://www.bostonscientific.com/en-US/products/stents--coronary/promus-premier-stent-system.html.

Mory et al., "Comparison of five one-step reconstruction algorithms for spectral CT. HAL, Archives Ouvertes", Physics in Medicine & Biology, 63, (2018) 235001.

Brendel et al. entitled "Empirical, projection-based basis-component decomposition method", Medical Imaging (2009), Physics of Medical Imaging, edited by Ehsan Samei and Jiang Hsieh, Proc. of SPIE vol. 7258.

International Search report and Written Opinion of PCT/EP2021/070004, dated Oct. 27, 2021.

\* cited by examiner

X-RAY POSITION TRACKING

CROSS-REFERENCE TO PRIOR APPLICATIONS

This application is the U.S. National Phase application under 35 U.S.C. § 371 of International Application No. PCT/EP2021/070004, filed on Jul. 16, 2021, which claims the benefit of European Patent Application No. 20188576.1, filed on Jul. 30, 2020. These applications are hereby incorporated by reference herein.

TECHNICAL FIELD

The present disclosure relates to position tracking during X-ray imaging. A spectral X-ray imaging system, a computer-implemented method, and a computer-readable storage medium are disclosed. A related interventional instrument, a kit including a plurality of interventional instruments, and an implantable device are also disclosed.

BACKGROUND

Spectral X-ray computed tomography "CT" imaging systems generate tomographic images that are used to perform medical investigations. In contrast to X-ray CT imaging systems, spectral X-ray CT imaging systems measure X-ray attenuation in multiple energy intervals. By processing X-ray attenuation data from multiple energy levels, spectral X-ray CT imaging systems can discriminate between media that have similar X-ray attenuation values when measured within a single energy interval, and which would be indistinguishable in X-ray CT images.

Various dual- and multi-energy X-ray CT imaging systems have been developed to generate spectral X-ray CT image data. Systems that employ temporally-sequential scanning with different energy X-rays, rapid kVp switching of the x-ray tube potential, multilayer detectors, dual X-ray sources, and photon counting detectors, have been developed.

Various material decomposition algorithms and image reconstruction algorithms have also been developed in order to process the spectral X-ray CT image data, and thereby generate spectral images in which different materials are distinguished. These include techniques disclosed in a document by Brendel, B. et al. entitled "Empirical, projection-based basis-component decomposition method", Medical Imaging 2009, Physics of Medical Imaging, edited by Ehsan Samei and Jiang Hsieh, Proc. of SPIE Vol. 7258, 72583Y; and techniques disclosed in a document by Mory, C. et al. entitled "Comparison of five one-step reconstruction algorithms for spectral CT"; Physics in Medicine and Biology, IOP Publishing, 2018, 63(23), pp.235001.

In a spectral X-ray CT imaging system, spectral image data representing attenuation of X-rays traversing an imaging region between the X-ray source and the X-ray detector is generated for multiple energy intervals of the X-rays whilst rotating the source and detector around an imaging region. The rotational frequency may be approximately 1 Hz or more. The spectral image data is then reconstructed into image slices, i.e. "tomographic" images, which may be stacked to provide a volumetric or "three-dimensional" image. Spectral X-ray CT imaging has for example been used in diagnostic imaging procedures to provide volumetric images that discriminate between a contrast agent and tissue, thereby permitting an accurate measurement of the contrast agent in the tissue.

By contrast, interventional procedures such as catheterization and stenting are typically performed using conventional X-ray imaging systems. In contrast to X-ray CT imaging systems, conventional X-ray imaging systems used in interventional procedures typically employ a support structure that can rotate an X-ray source and an X-ray detector around two or more orthogonal axes. The X-ray source and detector are mounted to the support structure in opposing positions in order to image an imaging region between them. The multiple degrees of freedom provided by the support structure permit the generation of image data from a desired orientation with respect to a patient's anatomy. During an interventional X-ray imaging procedure, the support structure is typically maintained in a static position with respect to a patient whilst single, or live, X-ray projection images are generated. Tomographic images may be generated by rotating the support structure, and thus the X-ray source and X-ray detector, around the patient whilst acquiring image data from multiple different orientations. The image data is then reconstructed in order to generate the tomographic image. Support structures having various shapes have been used, including for example a C-arm, an O-arm, and a U-shaped arm.

During an interventional X-ray imaging procedure there is often a need to perform position tracking. Position tracking may be used to localize a portion of the anatomy, or objects such as interventional instruments and implantable devices which might be hard to visualize under X-ray or difficult to distinguish from other image features. For example, interventional instruments such as guidewires include dense materials that strongly attenuate X-rays and are clearly visible in X-ray images, yet often difficult to distinguish from overlapping image features arising from other strong X-ray attenuating media such as bone. Interventional instruments that include less dense materials such as polymers are typically poorly visible under X-ray imaging. Implantable devices such as vascular stents may likewise be formed from metals or polymers and suffer from similar issues.

Various techniques have been developed for tracking portions of the anatomy, interventional instruments and implantable devices in the body. These include the use of fiducial markers, electromagnetic "EM" tracking, and fiber optic shape sensing systems that help to determine a position of the interventional device within a three-dimensional space.

However, there remains room to improve the tracking of portions of the anatomy and objects such as interventional instruments and implantable devices, when performing interventional X-ray imaging procedures.

SUMMARY

According to a first aspect of the present disclosure, a spectral X-ray imaging system is provided. The spectral X-ray imaging system includes an X-ray source, an X-ray detector, a support structure, and one or more processors. The X-ray source and the X-ray detector are mounted to the support structure, and configured to generate spectral image data representing attenuation of X-rays traversing an imaging region between the X-ray source and the X-ray detector, for each of three or more energy intervals of the X-rays. The support structure is configured to rotate the X-ray source and the X-ray detector around two or more orthogonal axes. The one or more processors are configured to cause the system to perform operations, comprising: generating a spectral image based on the spectral image data; and identifying, in the spectral image, a position of a first fiducial marker comprising a first material, based on a first X-ray absorption k-edge energy value of the first material. According to a second aspect of the present disclosure, a position of a second fiducial marker comprising a second material is identified in the spectral image, based on a second X-ray absorption k-edge energy value of the second material.

According to a third aspect of the present disclosure, the generating a spectral image comprises applying, in the projection domain, a material decomposition algorithm to the spectral image data to provide a first projection image representing the first material, and a second projection image representing a second material; and fusing the first projection image and the second projection image to provide the spectral image.

According to a fourth aspect of the present disclosure, the generating a spectral image comprises reconstructing a first volumetric image representing the first material; reconstructing a second volumetric image representing a second material; and fusing the first volumetric image and the second volumetric image to provide the spectral image.

According to a fifth aspect of the present disclosure, the generating a spectral image comprises generating first image data representing the first material, and generating second image data representing a second material. The identifying, in the spectral image, a position of a first fiducial marker and/or a position of a second fiducial marker, comprises applying a feature detection algorithm to the first image data and/or the second image data, respectively.

A related computer-implemented method, computer-readable storage medium, and computer program product are also provided in accordance with other aspects of the disclosure. Features disclosed in relation to the system may be incorporated into each of these aspects in a corresponding manner, and the features are not duplicated for each aspect for the sake of brevity. An interventional instrument, a kit including a plurality of interventional instruments, and an implantable device are also provided in accordance with other aspects of the disclosure.

Further features and advantages of the present disclosure will become apparent from the following description of preferred embodiments, given by way of example only, which is made with reference to the accompanying drawings.

DETAILED DESCRIPTION

Figure 1:
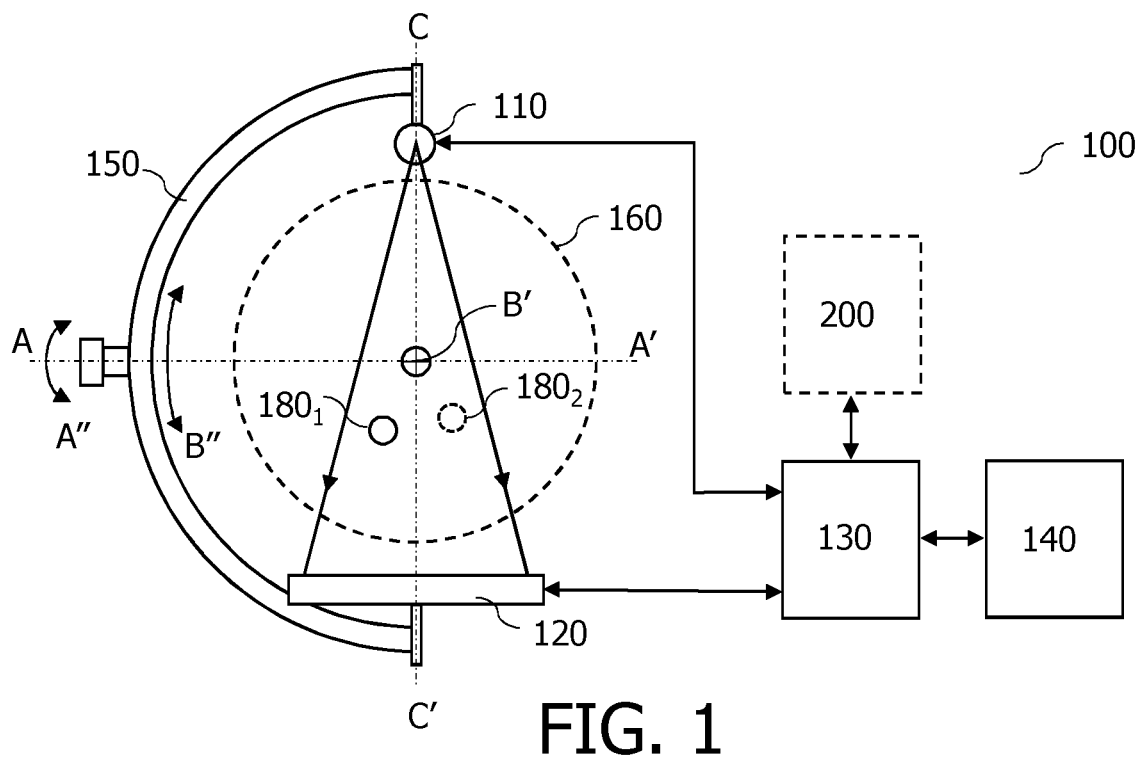
FIG. 1 illustrates a spectral X-ray imaging system 100 that includes an X-ray source 110, an X-ray detector 120, and a support structure 150 in accordance with some aspects of the disclosure.

FIG. 1 illustrates a spectral X-ray imaging system 100 that includes an X-ray source 110, an X-ray detector 120, and a support structure 150 in accordance with some aspects of the disclosure. The X-ray source 110 and the X-ray detector 120 are mounted to the support structure 150. The X-ray source 110 and X-ray detector 120 are separated so as to provide an imaging region 160 therebetween. X-rays emitted by the X-ray source 110 are detected by the X-ray detector 120, the extent of which is indicated by the unidirectional arrows in FIG. 1. The X-ray detector 110 receives the X-rays that have traversed the imaging region 160, and measures their intensity. Any X-ray attenuating media within the imaging region 160 will affect the measured intensity. In so doing, the X-ray detector 120 generates data representing the attenuation of X-rays traversing the imaging region 160.

The support structure 150 illustrated in FIG. 1 is a so-called "C-arm". A C-arm is a C-shaped example of a support structure for supporting the X-ray source and the X-ray detector. Support structures with alternative shapes might also be used in place of the illustrated C-arm, such as an O-shaped arm "O-arm", and a U-shaped arm "U-arm". The X-ray source 110 and X-ray detector 120 are mounted to the support structure 150. The support structure 150 is movable such that it can rotate the X-ray source 110 and the X-ray detector 120 around two or more orthogonal axes. For example, the support structure 150 can rotate the X-ray source 110 and the X-ray detector 120 around the axis A-A', and around the axis B' as indicated by the corresponding arrows A" and B" in FIG. 1. The axis B' is directed perpendicularly into the plane of the drawing. The support structure 150 might also rotate the X-ray source 110 and the X-ray detector 120 around a third axis, C-C' in FIG. 1, although this is not essential. The axes A-A', B', and C-C' are illustrated as intersecting in FIG. 1, although this is not essential and in some examples the axes do not intersect. The support structure 150 may be provided with various bearings and/or movable joints and/or hinges and/or other movable couplings in order to provide the desired movements.

The movement provided by support structure 150 allows the orientation of X-ray source 110 and X-ray detector 120 to be changed with respect to imaging region 160. In particular, the ability to rotate the X-ray source 110 and the X-ray detector 120 around two or more orthogonal axes facilitates its use in interventional imaging procedures. Image data may be acquired using X-ray source 110 and X-ray detector 120 with the source and detector in a desired static orientation with respect to imaging region 160. Live, or single projection images representing X-ray attenuation in imaging region 160 may be generated from the image data. Alternatively, image data may be acquired whilst rotating X-ray source 110 and X-ray detector 120 around axis A-A' or axis B'. The rotation may be continuous or stepped. The image data acquired in this manner may then be reconstructed into a tomographic image representing X-ray attenuation in imaging region 160.

In general, the size of the imaging region 160 is sufficient to accommodate an object to be imaged. The object may for example be a portion of a human or animal body. In some examples, imaging region 160 may accommodate a torso of a human body. Various factors affect the size of the imaging region 160, including the separation between the X-ray source 110 and X-ray detector 120, the profile of the beam of X-rays emitted by the X-ray source 110, the shape of the X-ray detector, and the range of movement of the support structure 150. By suitably adjusting these factors, the size and shape of imaging region 160 may be defined.

The X-ray source 110 and the X-ray detector 120 in FIG. 1 are configured to generate spectral image data. The spectral image data represents the attenuation of X-rays traversing the imaging region 160 between the X-ray source 110 and the X-ray detector 120, for each of three or more energy intervals of the X-rays. The spectral image data may be provided by various configurations of X-ray source 110 and X-ray detector 120. In general, the X-ray source 110 may include one of more monochromatic or polychromatic sources, and the X-ray detector 120 may include: a common detector for all X-ray energy intervals, or a multi-layer detector, or a photon counting detector. A multi-layer detector and a photon counting detector provide X-ray energy interval discrimination as described below. The X-ray source 110 may be controlled in order to emit X-rays within different X-ray energy intervals in a temporally-sequential manner.

The use of a linear or two-dimensional array of detector elements in X-ray detector 120 is contemplated. A linear array of detector elements may be used to generate spectral image data representing a tomographic image by continuous or stepped rotation of the X-ray source 110 and X-ray detector 120 around the imaging region 160, thereby generating spectral image data from multiple orientations with respect to the imaging region 160. The spectral image data may then be reconstructed into a tomographic image. A volumetric image may be generated by stacking tomographic images that are acquired at different axial positions in the imaging region 160. A two-dimensional array of detector elements may be rotated in a similar manner in order to generate spectral image data representing a tomographic or volumetric image. A two-dimensional array of detector elements may alternatively be maintained in a static position with respect to the imaging region 160 in order to generate spectral image data representing a projection image. Live, or single projection images may be generated with a two-dimensional array of detector elements in a static position, for example during a C-arm fluoroscopy imaging procedure.

In some examples, the X-ray detector 120 is a scintillator-type detector. Scintillator-type detectors use scintillator materials such as Gadolinium Oxysulfide "GOS", to convert each received X-ray into a burst of light which is then converted into an electrical signal using a photodetector. In other examples, the X-ray detector 120 is a so-called direct-conversion detector. In contrast to scintillator-type detectors, direct-conversion detectors use materials such as CZT or CdTe to convert received X-rays into a cloud of electron-hole pairs, thereby generating an electrical signal without the intermediate step of converting the X-rays to scintillation light. In some examples, scintillator-type detectors or direct-conversion detectors are stacked along the direction in which X-rays are received. In such a stacked, or "multi-layer" detector, the layer in which each X-ray is detected is dependent on its energy. The detector layers discriminate between different energy intervals of the X-rays, thereby providing spectral data on the received X-rays. Multilayer detectors are capable of detecting X-rays from multiple X-ray energy intervals simultaneously. In some examples, X-ray detector 120 generates its electrical output by integrating the scintillation light, or by integrating the electrical signal resulting from the cloud of electron-hole pairs. In some examples, the X-ray detector 120 is a photon counting detector. A photon counting detector provides spectral data on the received X-rays by binning each received X-ray photon into one of multiple energy intervals. The relevant energy interval is determined for each received X-ray photon from the pulse height induced by the electron-hole pairs that are generated in response to its absorption in a direct-conversion material. A photon counting detector can therefore detect X-rays from multiple X-ray energy intervals almost simultaneously.

In one example, X-ray source 110 in FIG. 1 is controlled by means of its X-ray tube potential to generate X-rays within each of three or more X-ray energy intervals. The X-ray tube potential is modulated between three different values in order to generate X-rays within each X-ray energy interval. The X-rays within each X-ray energy interval are therefore generated in a temporally sequential manner. This technique is known as kVp switching. X-rays may be generated within a different X-ray energy interval by changing the tube potential and/or filtering the X-ray spectrum before it traverses through the subject. In this example, the corresponding X-ray detector 120 may be common for all X-ray energy intervals. The spectral image data for a particular X-ray energy interval corresponds to the time at which X-rays are generated for that X-ray energy interval. In this example, the corresponding detector may alternatively be a multilayer detector, or indeed a photon counting detector.

In another example, X-ray source 110 in FIG. 1 includes multiple X-ray sources that are controlled to emit X-rays within three or more X-ray energy intervals in a temporally sequential manner. The corresponding detector may be common for all X-ray energy intervals. The spectral image data for a particular X-ray energy interval corresponds to the time at which X-rays are generated for that X-ray energy interval. In this example, the corresponding detector may alternatively be a multilayer detector, or indeed a photon counting detector.

In another example, X-ray source 110 in FIG. 1 includes one or more polychromatic sources. The polychromatic source(s) simultaneously generate(s) X-rays that have energies across the three or more energy intervals. A single polychromatic source may for example generate X-rays within three or more X-ray energy intervals that are distributed across the range 30 keV-120 keV. In this example, spectral image data is identified for each X-ray energy interval using a multi-layer detector or a photon counting detector.

Other combinations of the above X-ray sources and detectors may clearly also be used to provide the desired spectral image data for the three or more X-ray energy intervals.

The system 100 in FIG. 1 also includes one or more processors 130. The various items in FIG. 1 are in communication with one another as indicated by the interconnecting arrows. Thus, the one or more processor are in communication with the X-ray source 110 and the X-ray detector 120. The system 100 may also include one or more non-transitory computer-readable storage media 140, a display 200, and a user input device such as a keyboard and/or mouse (not indicated in FIG. 1). The one or more non-transitory computer-readable storage media 140 may collectively store instructions that, when executed by the one or more processors 130 cause the system 100 to perform various operations that are described in more detail below. In some examples the user input device may be used to provide user input to the system 100 in the form of instructions for executing the operations. The display 200 may be used to provide an image, to display the user input, and so forth.

In use, the support structure 150 in FIG. 1 is moved to a desired orientation with respect to an object within imaging region 160 in order to carry out an imaging procedure. The X-ray source 110 is controlled by the one or more processors 130 to generate X-rays as described in the examples above. The corresponding X-ray detector 120 generates spectral image data representing the attenuation of the X-rays traversing the imaging region 160 between the X-ray source 110 and the X-ray detector 120, for each of the three or more X-ray energy intervals. As described above, the spectral image data may be acquired with the X-ray source 110 and the X-ray detector 120 in a static orientation with respect to imaging region 160. Single, or live projection images representing X-ray attenuation in imaging region 160 may be generated from the spectral image data with the X-ray source 110 and X-ray detector 120 in this position. Alternatively, spectral image data may be acquired whilst rotating X-ray source 110 and X-ray detector 120 around axis A-A' or axis B'. The rotation may be continuous, or stepped, and controlled by the one or more processors 130. The spectral image data acquired in this manner may then be reconstructed into a tomographic image representing X-ray attenuation in imaging region 160. The image(s) may then be displayed on the display 200.

The inventors have determined that, by suitable processing of the spectral image data generated by the system 100 described above in relation to FIG. 1, it is possible to identify, in a spectral image, a position of a fiducial marker that includes a material having an X-ray absorption k-edge energy value. The processing performed by the one or more processors 130 in FIG. 1, includes the operations:

generating a spectral image based on the spectral image data;

identifying, in the spectral image, a position of a first fiducial marker $180_1$ comprising a first material, based on a first X-ray absorption k-edge energy value $190_1$ of the first material; and identifying, in the spectral image, a position of a second fiducial marker $180_2$ comprising a second material, based on a second X-ray absorption k-edge energy value $190_2$ of the second material, the second X-ray absorption k-edge energy value being different than the first X-ray absorption k-edge energy value.

Since these operations are provided in the system 100 that includes a support structure 150 that can rotate the X-ray source 110 and the X-ray detector 120 around two or more orthogonal axes, the system 100 may be used to track the position of the fiducial markers $180_{1,2}$ in an interventional imaging procedure.

Objects such as interventional instruments and implantable devices that include fiducial markers $180_{1,2}$ may therefore be tracked using the system 100 in a reliable manner. Additional operations may also be performed by the one or more processors 130 in FIG. 1, as described in more detail below.

In accordance with the present disclosure, spectral image data is generated, and a position of first and second fiducial markers that include a first material having a first X-ray absorption k-edge energy value and a second material having a second, different, X-ray absorption k-edge energy value, are identified in the spectral image. A spectral image in this context refers to an image that distinguishes between at least two materials using X-ray attenuation data from multiple X-ray energy intervals. In some examples the spectral images distinguishes between more than two materials, for example it may distinguish between three or more materials. In accordance with the present disclosure, the first material is provided by the first fiducial marker and the second material is provided by the second fiducial marker.

In one example, a further material may be distinguishable in the spectral images. The further material is a composite body material that includes a plurality of materials that are often present in the human body. The plurality of materials may include one or more of: bone, (soft) tissue, water, air, metal, contrast agent, and so forth. Thus, in this example, in the spectral image, the materials of the first fiducial marker and the second fiducial marker are distinguished from a composite body material. In another example, the further material is a more specific material within the composite body material, such as, (soft) tissue, bone, water, air, contrast agent, metal, and so forth. The further material may also be classified with a particular pathological state, such as (e.g. breast or lung) tumor tissue, vascular plaque, a renal stone, and so forth. Thus, in these examples, in the spectral image the first material of the first fiducial marker and the second material of the second fiducial marker may be distinguished from e.g. breast tumor tissue.

In another example, the second material has a second X-ray absorption k-edge energy value $190_2$, and a position of a second fiducial marker $180_2$ comprising the second material is identified in the spectral image, based on the second X-ray absorption k-edge energy value $190_2$ of the second material. The second X-ray absorption k-edge energy value $190_2$ of the second material is different to the first X-ray absorption k-edge energy value $190_1$ of the first material. In this example, in the spectral image the first material of the first fiducial marker is discriminated from the second material of the second fiducial marker.

In any of these examples, the spectral image may discriminate third and further materials, such as the example materials mentioned above, from the first and second materials. For example, the spectral image may discriminate between the first and second materials of the first and second fiducial markers, a third material such as bone, and a fourth material such as tissue. In general, generating the spectral image may include shading, color-coding, segmenting, or labelling, portions of the spectral image according to the material represented. Other techniques identifying different materials in the spectral image may also be used.

Various techniques may be used to generate the spectral image. In general, the X-ray attenuation spectrum of a material includes a contribution from Compton Scatter and a contribution from the Photo-electric effect. The attenuation due to Compton scatter is relatively similar for different materials, whereas the attenuation from the Photo-electric effect is strongly material-dependent. Both Compton Scatter and the Photo-electric effect exhibit an energy dependence; an effect that is exploited in spectral X-ray CT imaging systems in order to distinguish between different materials. Materials having a k-edge energy value exhibit a sharp increase in their X-ray attenuation spectra at X-ray energies corresponding to the k-edge energy value. The k-edge energy is defined as the minimum energy required for the Photo-electric event to occur with a k-shell electron, and occurs at a characteristic energy for each material. Materials having a k-edge energy value that is within the range of X-ray energies used in diagnostic X-ray imaging, i.e. approximately 30-120 keV, are suitable for use in system 100. For example, metals such as gadolinium, gold, platinum tantalum, and holmium each have a k-edge energy value within this range. By including such materials in a fiducial marker, the presence of these materials, and consequently the position of the fiducial marker, may be distinguished from other materials in the spectral image generated by the system 100.

Figure 2:
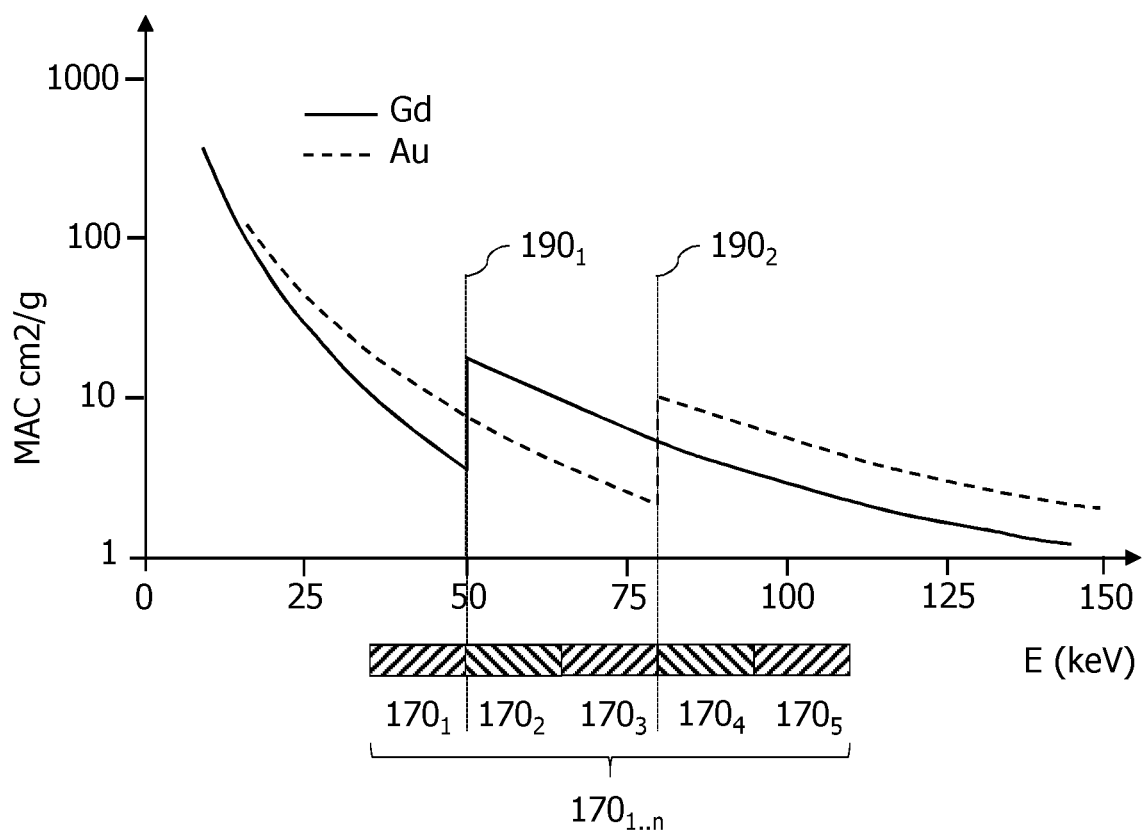
FIG. 2 is a graph illustrating the dependence of the mass attenuation coefficient MAC with X-ray energy for two example materials, gadolinium and gold.

FIG. 2 is a graph illustrating the dependence of the mass attenuation coefficient MAC with X-ray energy for two example materials, gadolinium and gold. The X-ray energy is indicated in FIG. 2 as label E and is measured in kilo electron-volts, keV. These example materials have characteristic k-edge energy values of 50.2 keV and 80.7 keV respectively, which gives rise to the sharp increase in their mass attenuation coefficients at k-edge values $190_1$ and $190_2$. Platinum, at 78.4 keV, tantalum, at 67.4 keV, and holmium, at 55.6 keV have different k-edge energy values to those illustrated in FIG. 2, and likewise exhibit a sharp increase in their mass attenuation coefficients.

FIG. 2 also illustrates a plurality of X-ray energy intervals $170_{1\ldots n}$ within which spectral X-ray image data may be generated. In the example illustrated in FIG. 2, five X-ray energy intervals are shown. In general, in examples in accordance with the present disclosure, spectral X-ray image data may be generated within three or more X-ray energy intervals. As illustrated in FIG. 2, in some examples, one or more of the X-ray energy intervals $170_{1\ldots n}$ may be above the X-ray absorption k-edge energy value $190_1$, $190_2$ of the material that is to be detected, and one or more of the X-ray energy intervals $170_{1\ldots n}$ may be below the X-ray absorption k-edge energy value. It is therefore noted that the energy intervals may have different energy intervals to those illustrated in FIG. 2, and that the energy intervals may be non-contiguous, and that the energy intervals may overlap.

In one example technique, a material decomposition algorithm is applied to the spectral image data to generate projection images. In this example, generating a spectral image comprises:

applying, in the projection domain, a material decomposition algorithm to the spectral image data to provide a first projection image representing the first material, and a second projection image representing a second material; and fusing the first projection image and the second projection image to provide the spectral image.

In this example technique, the support structure 150 in FIG. 1 is maintained in a stationary position whilst the spectral image data is generated. The spectral image data may be acquired using a two-dimensional array of detector elements. Single, or live X-ray projection images may be generated in this manner. Example material decomposition algorithms for this purpose, and the selection energy intervals, are disclosed in the document by Brendel, B. et al. entitled "Empirical, projection-based basis-component decomposition method", Medical Imaging 2009, Physics of Medical Imaging, edited by Ehsan Samei and Jiang Hsieh, Proc. of SPIE Vol. 7258, 72583Y.

In one example, projection images may for example be generated using the above technique with five energy intervals to decompose the spectral image data into four separate materials. The four materials include soft tissue and water, i.e. two materials that are typically present in the human body, and two materials having different k-edge values: gadolinium and gold.

Material decomposition algorithms that use fewer than five energy intervals may also be used. In practice, spectral imaging requires three or more energy intervals in order to decompose a spectral image into its photo-electric, Compton, and k-edge contributions and thereby distinguish a material having a k-edge energy value from body materials such as bone, (soft) tissue, water, air, metal, contrast agent, and so forth that are typically present in an X-ray image of the human anatomy.

Fusion of the images may be performed by combining spatially-corresponding pixel values in the images, for example by overlaying the images with a controlled transparency.

In one example, a material decomposition algorithm is applied selectively to the spectral image data to generate the projection images. In this example, a live stream of projection images is generated by the system 100, including a current projection image and a subsequent projection image. The position of the first fiducial marker is identified in the current projection image by applying the material decomposition algorithm to the spectral image data for the current projection image, and the material decomposition algorithm is applied selectively to the spectral image data for the subsequent projection image to provide the subsequent projection image by processing a region surrounding the expected position of the fiducial marker in the subsequent projection image. The selective processing may be used to alleviate the processing burden during, for example, fluoroscopy imaging.

In other example techniques, volumetric images are generated. The spectral image data may be acquired using a two-dimensional array of detector elements. In these examples, generating a spectral image comprises:

reconstructing a first volumetric image representing the first material;

reconstructing a second volumetric image representing a second material; and fusing the first volumetric image and the second volumetric image to provide the spectral image.

In these example techniques, the spectral image data is generated from multiple orientations with respect to imaging region 160 by rotating the support structure 150 around axis A-A' or axis B' in FIG. 1. The rotation may be in a continuous or stepped manner. Spectral images generated in this manner may be reconstructed into a tomographic or volumetric image, and facilitate a distinction between fiducial markers that might otherwise overlap on a projection image. Implantable devices such as biopsy markers, or attached brachytherapy seeds, or interventional devices such as guidewires that include such fiducial markers may for example be more easily distinguished in such images. Fusion of the images may be performed by combining spatially-corresponding voxel values in the images, for example by overlaying the images with a controlled transparency.

In these examples the step of fusing the volumetric images may also include:

forward projecting the first volumetric image and the second volumetric image to provide the spectral image as a projection image.

The forward projecting may include forward projecting the images onto a plane parallel with the X-ray detector 120, or another plane. The discrimination provided by the k-edge energy value(s) of the fiducial marker(s) permits a distinction between fiducial markers that might otherwise overlap in a projection image.

Various image reconstruction techniques are contemplated for reconstructing the volumetric images.

In one example technique, generating a spectral image comprises:

applying, in the projection domain, a material decomposition algorithm to the spectral image data to provide first sinogram data representing the first material, and second sinogram data representing the second material;

reconstructing the first volumetric image from the first sinogram data;

reconstructing the second volumetric image from the second sinogram data;

and wherein reconstructing the first volumetric image and reconstructing the second volumetric image comprises applying a filtered back-projection algorithm to the first sinogram data and to the second sinogram data respectively.

The material decomposition algorithms mentioned above may be used with any of these techniques in order to discriminate between different materials. In one example implementation the position of a platinum-coated stent is identified. In this implementation, volumetric images are generated using five energy intervals of photon-counting data as input to a maximum-likelihood material decomposition algorithm in the projection domain, to identify for each pixel the attenuation length through three materials, water, iodine, and platinum, with highest probability under the Poisson noise model. Afterwards, the three material sinograms are reconstructed separately with a filtered back-projection algorithm. One of the resulting images is a material-selective platinum-image, i.e. a k-edge image, in which the platinum coating of the stent is separated from the materials water and iodine that are present in a typical contrast-enhanced X-ray image of the human anatomy.

In another example technique, generating a spectral image comprises:
  reconstructing an energy channel image for each of the plurality of energy intervals $170_{1...n}$; and
  generating the first volumetric image and the second volumetric image from the reconstructed energy channel images using a material decomposition algorithm; and wherein generating the first volumetric image and the second volumetric image is based on first calibration data representing attenuation of the X-rays by a first object comprising the first material, and second calibration data representing attenuation of the X-rays by a second object comprising the second material, and wherein the first object and the second object are disposed in known positions in the imaging region 160.

The material decomposition algorithms mentioned above may also be used here to discriminate between different materials. In one example, the calibration data is provided by disposing a sample of the first material and the second material in a patient support pallet, or on a surface of the patient's body. Since the position of the first and second objects are known, their corresponding spectral image data may be identified and used in order to provide the calibration data.

In another example technique, generating a spectral image comprises:
  using an iterative one-step inversion algorithm to simultaneously reconstruct the first volumetric image and the second volumetric image.

Example reconstruction algorithms for this purpose, and the selection of energy intervals, are disclosed in the document by Mory, C. et al. entitled "Comparison of five one-step reconstruction algorithms for spectral CT"; Physics in Medicine and Biology, TOP Publishing, 2018, 63(23), pp.235001.

Irrespective of whether projection images, or volumetric images are generated, further operations may also be carried out by system 100, as described below.

In some examples, the position of the first fiducial marker $180_1$ and/or the position of the second fiducial marker, are identified by means of a feature detection algorithm. In these examples, generating a spectral image comprises:
  generating first image data representing the first material, and generating second image data representing a second material; and
  wherein the identifying, in the spectral image, a position of a first fiducial marker $180_1$ and/or a position of a second fiducial marker, comprises applying a feature detection algorithm to the first image data and/or the second image data, respectively.

The first image data may represent the first projection image or the first volumetric image, and the second image data may represent the second projection image or the second volumetric image. The use of various feature detection algorithms in these examples is contemplated. In one example, applying a feature detection algorithm to the first image data and/or the second image data, comprises:
  analyzing the first data and/or the second image data, to determine a position in the spectral image corresponding to a maximum image intensity in the first image data and/or the second image data, respectively.

Using the maximum intensity in this manner provides an accurate indication of the marker position.

In another example, applying a feature detection algorithm to the first image data and/or the second image data, comprises:
  analyzing the first image data and/or the second image data, to determine a position in the spectral image corresponding to a predetermined image intensity pattern in the first image data and/or the second image data, respectively.

The predetermined image intensity pattern in this example corresponds to an expected pattern of the fiducial marker. For example, if the fiducial marker(s) is provided by the first material or the second material in the form of a wire or disc having a circular shape; the expected pattern would be a circle. Fiducial markers having different shapes may be identified in a similar manner. Likewise, if the fiducial marker is provided in the form of multiple elements formed of the first material or the second material, the expected pattern of the multiple elements would be used.

In another example, applying a feature detection algorithm to the first image data and/or the second image data, comprises:
  analyzing the first image data and/or the second image data, to determine a position and/or orientation in the spectral image of an interventional instrument or an implantable device comprising the first fiducial marker $180_1$ and the second fiducial marker $180_2$ respectively, based on a model representing X-ray attenuation of the interventional instrument or the implantable device.

The model in this example may represent the shape of the fiducial marker(s). For example, the marker may be provided in the form of multiple platinum wires that together form part or all of a cardiovascular stent. In this case the model might represent the expected X-ray attenuation in a platinum-specific spectral image, optionally together with the attenuation that might be expected in other material-specific images. By analyzing the image data to determine a match with the model, a position, and optionally a spatial orientation, of the fiducial marker in the spectral image may be determined.

The fiducial markers $180_1$, $180_2$ described above may be provided in various forms, and attached to various objects. The fiducial markers may be provided in any shape. For example, a fiducial marker may be provided by a cylinder, a sphere, a spiral, a disc, or another shape. The fiducial marker, or a portion thereof, may be formed from, or coated with, the material having the relevant k-edge energy value. In one example a fiducial marker may be plated with gold or platinum. The fiducial marker may be implantable or attachable to a surface of the body.

Figure 3:
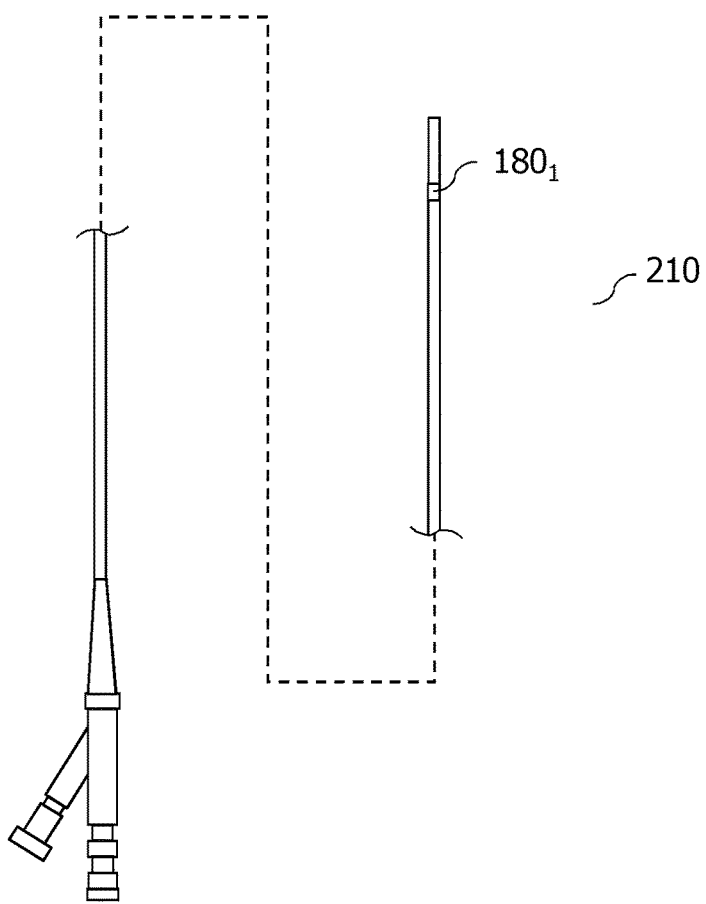
FIG. 3 illustrates an example of an interventional instrument 210 in the form of an IVUS catheter including a first fiducial marker $180_1$.

In some examples, the fiducial marker(s) $180_1$, $180_2$ are provided on an interventional instrument. The interventional instrument may be used with the system 100 in FIG. 1, or a spectral X-ray CT imaging system. In general, the position of interventional instruments may be difficult to determine under X-ray imaging. When formed from metals, the appearance of interventional instruments may be obscured by other strong X-ray attenuation media such as bone. This issue is particularly acute during projection imaging. When formed from polymers, interventional instruments may be invisible under X-ray imaging. FIG. 3 illustrates an example of an interventional instrument 210 in the form of an IVUS catheter including a first fiducial marker $180_1$. With reference to FIG. 3, the interventional instrument 210 includes at least one fiducial marker. The at least one fiducial marker includes a first fiducial marker $180_1$ comprising a first material having a first X-ray absorption k-edge energy value $190_1$. The first fiducial marker $180_1$ may for example be a platinum coating that is applied to a portion of the shaft of the IVUS catheter. The interventional instrument 210 may include one or more additional fiducial markers.

In certain embodiments, the interventional instrument 210 includes a second fiducial marker $180_2$ comprising a second material having a second X-ray absorption k-edge energy value $190_1$. The second material, and second X-ray absorption k-edge energy value $190_2$ are different to the first material, and first X-ray absorption k-edge energy value $190_1$, and thus permit a distinction between the markers and their positions on the interventional instrument 210. The instrument may therefore be more readily located and/or its orientation may be determined.

In another example, the interventional instrument 210 may include a plurality of first fiducial markers $180_1$ and/or a plurality of second fiducial markers $180_2$. By providing the fiducial marker(s) on the interventional instrument 210, its visibility in a spectral image may therefore be improved. The fiducial marker(s) may be attached to other interventional instruments than the example IVUS catheter, for example it may be attached to a catheter in general, a guidewire, a balloon such as an angioplasty balloon or a cutting balloon, an atherectomy device, a thrombectomy system, an atrial appendage closure device, an aortic valve placement system, or to an instrument used in a fractional flow reserve "FFR" measurement, an optical coherence tomography "OCT" imaging instrument, a near infrared spectroscopy "NIRS" imaging system and so forth.

Interventional instruments that include the fiducial marker(s) may also be provided in the form of a kit. A kit may include a first interventional instrument 210 and a second interventional instrument. The kit may be used with the system 100 in FIG. 1, or a spectral X-ray CT imaging system. In the kit, a first interventional instrument 210 includes a first fiducial marker $180_1$ comprising a first material having a first X-ray absorption k-edge energy value $190_1$, and a second interventional instrument includes a second fiducial marker $180_2$ comprising a second material having a second X-ray absorption k-edge energy value $190_2$. Interventional instruments from the kit may be used together during an imaging procedure and distinguished from one another by means of their fiducial markers. The kit may for example include two or more intravascular catheters.

Figure 4:
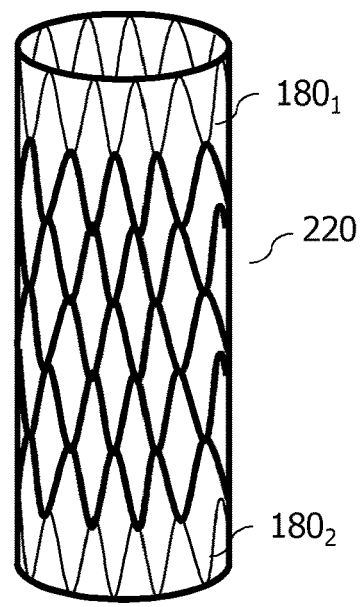
FIG. 4 illustrates an example of an implantable device 220 in the form of a stent including a first fiducial marker $180_1$ and a second fiducial marker $180_2$.

The fiducial markers $180_1$, $180_2$ may alternatively be provided on an implantable device. The implantable device may be used with the system 100 in FIG. 1, or a spectral X-ray CT imaging system. FIG. 4 illustrates an example of an implantable device 220 in the form of a stent that includes a first fiducial marker $180_1$ and a second fiducial marker $180_2$. In general, an implantable device 220 may include a plurality of fiducial markers: a first fiducial marker $180_1$ comprising a first material having a first X-ray absorption k-edge energy value $190_1$, and a second fiducial marker $180_2$ comprising a second material having a second X-ray absorption k-edge energy value $190_2$.

By providing multiple fiducial markers having different k-edge energy values on an implantable device such as a stent, the orientation of the implantable device may be determined in a spectral image. The fiducial markers may be attached to the stent, or alternatively form part of the stent, as indicated by the fiducial markers $180_1$ and $180_2$ in FIG. 4. For example, the fiducial markers $180_1$ and $180_2$ may be provided in the form of e.g. platinum wires within the stent structure or a platinum coating on the stent. In one example, and as illustrated in FIG. 4, a fiducial marker $180_1$ may be attached to a proximal end of a vascular stent, and another fiducial marker $180_2$ may be attached to the distal end of the vascular stent. Attaching multiple fiducial markers having different k-edge energy values to an implantable device such as a stent in this manner may help to distinguish overlapping stents in a projection image, and also help to identify each end of the stent. It may also help to distinguish between a stent that is currently being implanted and a previously-implanted.

The fiducial markers may be attached to other implantable devices than the example stent given above, for example, they may be attached to a biopsy marker, a brachytherapy seed, a pacemaker lead, a heart valve replacement, a ventricular assist device, a wireless cardiac monitor, an intravascular defibrillator, a neurostimulator, a brain-computer interface, a drug delivery injector, and so forth. Biopsy markers are often the size of sesame seed and are used to mark the location where tissue samples have been taken, for example in breast cancer diagnosis. By providing a biopsy marker with different k-edge materials or different spectral attenuation, the biopsy marker can be better distinguished from other biopsy markers in close spatial proximity but with different properties such as time of placement, radioactivity level and so forth. By providing brachytherapy seeds with such fiducial markers, their location, time of placement, and radioactivity levels may be better distinguished. Pacemaker leads often remain within the body and are not extracted when a pacemaker is removed or renewed because lead removal is a complex surgical procedure. The leads can stay attached to the heart permanently. Providing the pacemaker leads with the fiducials improves the distinction between a currently-implanted lead and a previously-implanted lead.

In another example, a computer-implemented method is provided. The computer-implemented method may be used with the system 100 described above, and may therefore include functionality corresponding to that described above in relation to system 100. For brevity, not all details of the system 100 are duplicated here in relation to the method. The method may be provided as a non-transitory computer-readable storage medium comprising a set of computer-readable instructions stored thereon which, when executed by at least one processor, cause the at least one processor to perform the method. In other words, the above-described methods may be implemented as a computer program product. The computer program product can be provided by dedicated hardware or hardware capable of running the software in association with appropriate software. When provided by a processor, these functions can be provided by a single dedicated processor, a single shared processor, or multiple individual processors that some of the processors can share. Moreover, the explicit use of the terms "processor" or "controller" should not be interpreted as exclusively referring to hardware capable of running software, and can implicitly include, but is not limited to, digital signal processor "DSP" hardware, read only memory "ROM" for storing software, random access memory "RAM", a nonvolatile storage device, and the like. Furthermore, examples of the present disclosure can take the form of a computer program product accessible from a computer usable storage medium or a computer-readable storage medium, the computer program product providing program code for use by or in connection with a computer or any instruction execution system. For the purposes of this description, a computer-usable storage medium or computer-readable storage medium can be any apparatus that can comprise, store, communicate, propagate, or transport a program for use by or in connection with an instruction execution system, apparatus, or device. The medium can be an electronic, magnetic, optical, electromagnetic, infrared, or semiconductor system or device or device or propagation medium. Examples of computer-readable media include semiconductor or solid state memories, magnetic tape, removable computer disks, random access memory "RAM", read only memory "ROM", rigid magnetic disks, and optical disks. Current examples of optical disks include compact disk-read only memory "CD-ROM", optical disk-read/write "CD-R/W", Blu-Ray™, and DVD.

Thus, there is provided, a computer-implemented method of processing spectral image data representing attenuation of X-rays traversing an imaging region 160 between an X-ray source 110 and an X-ray detector 120, for each of three or more energy intervals $170_{1...n}$ of the X-rays. The method may be used with the system 100, and comprises:

generating a spectral image based on the spectral image data; and identifying, in the spectral image, a position of a first fiducial marker $180_1$ comprising a first material, based on a first X-ray absorption k-edge energy value $190_1$ of the first material.

Other operations described in relation to the system 100 may also be provided by the method. For example, the computer-implemented method may also include the applying of a material decomposition algorithm to the spectral image data to provide projection images, and the volumetric image reconstruction operations described above.

A non-transitory computer-readable storage medium is also provided. The non-transitory computer-readable storage medium is encoded with instructions executable by the one or more processors 130 for processing spectral image data representing attenuation of X-rays traversing an imaging region 160 between an X-ray source 110 and an X-ray detector 120, for each of three or more energy intervals $170_1...n$ of the X-rays. The computer-readable storage medium may be used to process spectral image data generated by the system 100, and comprises instructions to perform operations, comprising:

generating a spectral image based on the spectral image data; and identifying, in the spectral image, a position of a first fiducial marker $180_1$ comprising a first material, based on a first X-ray absorption k-edge energy value $190_1$ of the first material.

A computer program product is also provided. The computer program product comprises instructions, which when executed by a processor, such as a processor 130 of the system 100, cause the processor to carry out a method, comprising:

receiving spectral image data representing attenuation of X-rays traversing an imaging region 160 between an X-ray source 110 and an X-ray detector 120, for each of three or more energy intervals $170_1...n$ of the X-rays;

generating a spectral image based on the spectral image data; and identifying, in the spectral image, a position of a first fiducial marker $180_1$ comprising the first material, based on a first X-ray absorption k-edge energy value $190_1$ of the first material.

Other operations described in relation to the system 100 may also be provided by instructions of the computer program product, or by instructions of the non-transitory computer-readable storage medium.

The above examples are to be understood as illustrative examples of the present disclosure. Further examples are also envisaged. For example, the examples described in relation to system 100 may also be provided by the computer-implemented method, or by the computer program product or by the computer-readable storage medium. It is therefore to be understood that a feature described in relation to any one example may be used alone, or in combination with other features described, and may also be used in combination with one or more features of another of the examples, or a combination of other the examples. Furthermore, equivalents and modifications not described above may also be employed without departing from the scope of the disclosure, which is defined in the accompanying claims. Any reference signs in the claims should not be construed as limiting the scope of the disclosure.

The invention claimed is:

1. A spectral X-ray imaging system comprising:
an X-ray source and an X-ray detector configured to generate spectral image data representing attenuation of X-rays traversing an imaging region between the X-ray source and the X-ray detector, for each of three or more energy intervals of the X-rays;
a support structure is configured to rotate the X-ray source and the X-ray detector around two or more orthogonal axes; and
one or more processors configured to:
generate a spectral image based on the spectral image data,
identify, in the spectral image, a position of a first fiducial marker comprising a first material, based on a first X-ray absorption k-edge energy value of the first material, and
identify, in the spectral image, a position of a second fiducial marker comprising a second material, based on a second X-ray absorption k-edge energy value of the second material, the second X-ray absorption k-edge energy value being different to the first X-ray absorption k-edge energy value.

2. The spectral X-ray imaging system according to claim 1, wherein the spectral image discriminates between the first and second materials and at least a further material, and wherein the further material comprises: tissue, bone, water, air, contrast agent, or metal.

3. The spectral X-ray imaging system according to claim 1, wherein, to generate the spectral image, the one or more processors are further configured to:
apply, in a projection domain, a material decomposition algorithm to the spectral image data to provide a first projection image representing the first material, and a second projection image representing a second material; and
fuse the first projection image and the second projection image to provide the spectral image.

4. The spectral X-ray imaging system according to claim 1, wherein, to generate the spectral image, the one or more processors are further configured to:

reconstruct a first volumetric image representing the first material;
reconstruct a second volumetric image representing the second material; and
fuse the first volumetric image and the second volumetric image to provide the spectral image.

5. The spectral X-ray imaging system according to claim 4, wherein the fusing comprises forward projecting the first volumetric image and the second volumetric image to provide the spectral image as a projection image.

6. The spectral X-ray imaging system according to claim 4, wherein to generate the spectral image, the one or more processors are further configured to:
apply, in a projection domain, a material decomposition algorithm to the spectral image data to provide first sinogram data representing the first material, and second sinogram data representing the second material;
reconstruct the first volumetric image from the first sinogram data; and
reconstruct the second volumetric image from the second sinogram data;
and wherein reconstructing the first volumetric image and reconstructing the second volumetric image comprises applying a filtered back-projection algorithm to the first sinogram data and to the second sinogram data respectively.

7. The spectral X-ray imaging system according to claim 4, wherein to generate the spectral image, the one or more processors are further configured to:
reconstruct an energy channel image for each of the three or more energy intervals; and
generate the first volumetric image and the second volumetric image from the reconstructed energy channel image for each of the three or more energy intervals using a material decomposition algorithm;
and wherein generating the first volumetric image and the second volumetric image is based on first calibration data representing attenuation of the X-rays by a first object comprising the first material, and second calibration data representing attenuation of the X-rays by a second object comprising the second material, and wherein the first object and the second object are disposed in known positions in the imaging region.

8. The spectral X-ray imaging system according to claim 4, wherein the spectral image is generated using an iterative one-step inversion algorithm to simultaneously reconstruct the first volumetric image and the second volumetric image.

9. The spectral X-ray imaging system according to claim 1, wherein the spectral image is generated by generating first image data representing the first material, and generating second image data representing the second material; and
wherein the identifying, in the spectral image, the position of the first fiducial marker and the position of the second fiducial marker comprises applying a feature detection algorithm to the first image data and the second image data, respectively.

10. The spectral X-ray imaging system according to claim 9, wherein to apply the feature detection algorithm to the first image data and the second image data, the one or more processors is further configured to at least one of:
analyze at least one of the first image data or the second image data, to determine a position in the spectral image corresponding to a maximum image intensity in at least one of the first image data or the second image data, respectively; and
analyze at least one of the first image data or the second image data, to determine a position in the spectral image corresponding to a predetermined image intensity pattern in at least one of the first image data or the second image data, respectively.

11. The spectral X-ray imaging system according to claim 9, wherein to apply the feature detection algorithm to the first image data and the second image data, the one or more processors are further configured to:
analyze the first image data and the second image data; to determine a position and/or orientation in the spectral image of an interventional instrument or an implantable device comprising the first fiducial marker and the second fiducial marker respectively, based on a model representing X-ray attenuation of the interventional instrument or the implantable device.

12. The spectral X-ray imaging system according to claim 1, wherein the one or more processors are further configured to track a position of the first and second fiducial markers in an interventional imaging procedure.

13. An interventional instrument for use with the system according to claim 1, the interventional instrument comprising at least two fiducial markers comprising the first fiducial marker comprising the first material having the first X-ray absorption k-edge energy value and the second fiducial marker comprising the second material having the second X-ray absorption k-edge energy value, the second X-ray absorption k-edge energy value being different to the first X-ray absorption k-edge energy value.

14. A kit comprising a first interventional instrument and a second interventional instrument for use with the system according to claim 1;
wherein the first interventional instrument comprises the first fiducial marker comprising the first material having the first X-ray absorption k-edge energy value; and
wherein the second interventional instrument comprises the second fiducial marker comprising the second material having the second X-ray absorption k-edge energy value, the second X-ray absorption k-edge energy value being different to the first X-ray absorption k-edge energy value.

15. A computer-implemented method of processing spectral image data representing attenuation of X-rays traversing an imaging region between an X-ray source and an X-ray detector, the method comprising:
generating a spectral image based on the spectral image data;
identifying, in the spectral image, a position of a first fiducial marker comprising a first material, based on a first X-ray absorption k-edge energy value of the first material, and
identifying, in the spectral image, a position of a second fiducial marker comprising a second material, based on a second X-ray absorption k-edge energy value of the second material, the second X-ray absorption k-edge energy value being different to the first X-ray absorption k-edge energy value.

* * * * *